(12) United States Patent
Liu et al.

(10) Patent No.: US 8,846,592 B2
(45) Date of Patent: Sep. 30, 2014

(54) STABLE LIQUID CLEANSING COMPOSITIONS COMPRISING CRITICAL WINDOW OF HYDROGENATED TRIGLYCERIDE OILS

(75) Inventors: Hongjie Liu, Shelton, CT (US); Liang Sheng Tsaur, Norwood, NJ (US); Jamie Lynn Miller, New Haven, CT (US); Tirucherai Varahan Vasudevan, Bethany, CT (US); Virgilio Barba Villa, Emerson, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 805 days.

(21) Appl. No.: 12/904,571

(22) Filed: Oct. 14, 2010

(65) Prior Publication Data

US 2012/0094884 A1    Apr. 19, 2012

(51) Int. Cl.

| | |
|---|---|
| *A61Q 19/10* | (2006.01) |
| *A61K 8/36* | (2006.01) |
| *A61K 8/46* | (2006.01) |
| *A61K 8/92* | (2006.01) |
| *A61K 8/37* | (2006.01) |
| *A61K 8/44* | (2006.01) |

(52) U.S. Cl.
CPC ............... *A61Q 19/10* (2013.01); *A61K 8/361* (2013.01); *A61K 8/466* (2013.01); *A61K 8/922* (2013.01); *A61K 8/37* (2013.01); *A61K 8/44* (2013.01); *A61K 2800/596* (2013.01); *A61K 2800/52* (2013.01); *A61K 8/375* (2013.01)
USPC ........................................................ 510/159

(58) Field of Classification Search
USPC ........................................................ 510/159
See application file for complete search history.

(56) References Cited

U.S. PATENT DOCUMENTS

| 3,723,325 A | 3/1973 | Parran, Jr. |
|---|---|---|
| 4,565,647 A | 1/1986 | Llenado |
| 5,009,814 A | 4/1991 | Kelkenberg et al. |
| 5,389,279 A | 2/1995 | Au et al. |
| 5,464,554 A * | 11/1995 | Gu et al. ................. 510/130 |
| 6,395,690 B1 | 5/2002 | Tsaur |
| 2002/0012697 A1* | 1/2002 | Schwartz ................. 424/450 |
| 2004/0234467 A1 | 11/2004 | Ananthapadmanabhan et al. |
| 2004/0234468 A1 | 11/2004 | Kerschner et al. |
| 2004/0234469 A1 | 11/2004 | O'Connor et al. |
| 2004/0234558 A1 | 11/2004 | O'Connor et al. |
| 2004/0235691 A1 | 11/2004 | Pham et al. |
| 2005/0281851 A1 | 12/2005 | Cap |
| 2008/0081776 A1* | 4/2008 | Crotty et al. ............. 510/130 |
| 2008/0282601 A1* | 11/2008 | Luttke ....................... 44/275 |
| 2009/0012177 A1 | 1/2009 | Shafa et al. |

FOREIGN PATENT DOCUMENTS

| CA | 2678768 | | 8/2009 | |
|---|---|---|---|---|
| EP | 348976 A2 | | 1/1990 | |
| EP | 1479365 | | 11/2004 | |
| EP | 1479378 | | 11/2004 | |
| JP | WO-2009/064023 | * | 5/2009 | ........ A61K 8/97 |
| WO | WO9932069 | | 7/1999 | |
| WO | 2004/017745 | | 3/2004 | |
| WO | WO2009064023 A1 | | 5/2009 | |

OTHER PUBLICATIONS

Co-pending Application for Applicant: Liu et al.; U.S. Appl. No. 12/371,050, filed Feb. 13, 2009, entitled: Personal Wash Composition Comprising Specific Blends of Saturation (Hydrogenated) Oil to Unsaturated Triglyceride.
Co-pending Application for Applicant Liu et al.; U.S. Appl. No. 12/904,594, filed Oct. 14, 2010, entitled: Stable Liquid Cleansing Compositions Comprising Critical Window of Partially Hydrogenated Triglyceride Oil of Defined Iodine Value.
PCT International Search Report and Written Opinion on Application No. PCT/EP2011/066926 mailed Jul. 3, 2012.
Internet website article from Welch House Clark on "Refined Soybean Oil".

* cited by examiner

*Primary Examiner* — Bijan Ahvazi
*Assistant Examiner* — Thuy-Ai Nguyen
(74) *Attorney, Agent, or Firm* — Ronald A. Koatz

(57) ABSTRACT

The present invention provides personal wash compositions where hydrogenated triglyceride oils (defined by IV of 0 to <20) are specifically formulated to provide low temperature stability. Specifically when formulated to have specific concentration of hydrogenated triglycerides, delivered as pure sample or from mixtures of hydrogenated and other triglyceride oils, desirable low temperature stability of formulations is achieved.

4 Claims, No Drawings

STABLE LIQUID CLEANSING COMPOSITIONS COMPRISING CRITICAL WINDOW OF HYDROGENATED TRIGLYCERIDE OILS

FIELD OF THE INVENTION

The present invention relates to stable liquid personal wash compositions comprising long chain fatty acids (to provide skin functional benefits like mildness and moisturization) and hydrogenated triglycerides. The hydrogenated triglycerides (defined by Iodine Value (IV number) of 0 to less than 20) stabilize the compositions over a wide range of storage temperatures. More specifically, the hydrogenated (saturated) triglycerides prevent low temperature composition instability caused by high melting point components (long chain fatty acids, for example) found in the liquid cleansing formulations. Use of critical amounts (e.g., minimum to provide sufficient crystallinity to stabilize liquid, but not too much as to kill foam) of saturated triglycerides in liquid personal wash composition is believed unknown.

The hydrogenated triglyceride may be introduced into the formulations as a pure ingredient (only saturated components of defined IV included); or as mixture of pure ingredient in other oils (e.g., vegetable oil or mineral oil), as long as the hydrogenated triglycerides of defined IV are still used in the amounts required in the fully formulated personal wash composition. This amount is required to ensure the viscosity of the composition retains at least a defined certain percentage of its original viscosity (e.g., greater than 70%, preferably 75% or greater, even more preferably, 80% or greater of its original viscosity) following cold storage conditions (e.g., after kept at 4° C. for a one week period).

Measurement of the degree of saturation, whether introduced in the form of hydrogenated triglyceride of defined IV or as a mixture of such hydrogenated triglyceride with other oils can be conducted by thermal phase transition analysis (melting and crystallization), crystallinity analysis (e.g., differential scanning calorimetry), NMR relaxation study, or standard analytical titration method (indexed by Iodine Value, also know as IV value, refer ASTM D5768-02 and DIN 53241). Whether referring to the amounts of C=C double bonds, or ratio of saturated/unsaturated fatty acids in triglycerides, IV value is good easy way to identify saturated triglycerides (e.g., the lower the IV value, the more saturated).

In this application, applicants claim compositions having a critical window of saturated (hydrogenated) triglycerides (whether introduced as pure sample or as mixtures with other oils) which allow retention of stability for personal wash formulations. When noted amounts are used, personal wash compositions retain a defined percent of original viscosity. The saturated triglycerides contain a level of saturation yielding high melting point at room temperature. In applicants' copending application, critical window (amounts and defined IV) of partially hydrogenated triglycerides which have a level of saturation providing similar stability is described.

BACKGROUND

Personal wash compositions seek to provide consumers additional skin conditioning benefits beyond simple cleansing. The principal benefits provided by such compositions are mildness and moisturization. Because of their low cost, smooth sensory feel, and mildness to skin, emollient oils such as triglyceride based vegetable oils (e.g., soybean oil, sunflower seed oil) and fatty acids are among the most commonly used skin benefit agents.

Emollient oils such as triglycerides and long chain fatty acids can deposit or penetrate into skin from personal wash application to retard skin dehydration and alleviate skin irritation (skin lipid/protein damage) from surfactants. The emollient oils play these roles in body wash products because of their intrinsic water insoluble property (hydrophobicity). However, the oil phase in liquid cleansing formulations may increase the challenge to formulate stable liquid cleansing products because of the inherent incompatibility between aqueous continuous phase and the water immiscible oil phase. High levels of surfactants and/or emulsifiers are frequently used to stabilize the interface between aqueous phase and oil phase to help stabilize the formulations.

A problem in the art is how to provide long term stability over a wide range of transportation/storage temperatures. Surfactant based liquid cleanser formulations use different structuring technologies to form stable formulations. Simple isotropic formulations, for example, can be stabilized using high concentration of surfactant. More complex liquid cleansing formulations, which may contain substantial amounts of skin beneficial agents, use other structuring agents such as suspending polymer, fibers, starch, or solid long chain (>C12) fatty acids to help stabilize the formulations. In order to form a stable and consistent body wash product, usually the composition needs to be formulated at a temperature higher than the melting point of all ingredients in the compositions so that the highest melting solid ingredient can evenly distribute into the surfactant phase. When the temperature decreases below their melting point, however, the contained solid ingredients generally crystallize. Often, small crystal particles grow and precipitate out from the surfactant phase. This can cause both product phase separation and significant viscosity drop. Where the temperature is even lower than the Krafft point of the surfactant phase, co-crystallization of solid fatty acid and surfactant may occur when using solid hydrophobic ingredients.

In applicants' copending U.S. Ser. No. 12/371,050, filed in February 2009, there is disclosed a method of using fully hydrogenated triglyceride oil as a structuring agent to modify the rheology of liquid triglyceride oils. It was found that, within specifically defined ratios of hydrogenated triglycerides to liquid oils, an oil mixture of regular liquid vegetable oils and its hydrogenated derivatives could match the shear thinning property of petrolatum gel and have a negligible impact on the foaming property of liquid cleansing formulations. The IV of the blend is well above that of the saturated triglyceride of the subject invention, which suggests that there is not sufficient saturated triglyceride in the blend to obtain at least 70% viscosity of the original composition. There is further no recognized benefit (e.g., the stability) of our oils, e.g., based on sufficient level of hydrogenated triglyceride to provide required solidness. In a preferred embodiment of our invention, only saturated (hydrogenated) triglycerides are applied or, if used in mixture with other oils, 40% or more, preferably 50% or more of mix comprises saturated triglycerides.

Unexpectedly, applicants have now found that minimum amounts of hydrogenated triglyceride oils (introduced as pure sample or as mixtures with oil where preferably, >40%, more preferably 50% or more of mix is saturated) can stabilize the oil/water interface of liquid products containing fatty acid and thus stabilize the liquid cleansing formulations over a wide range of storage temperature, even temperatures as low as 4° C.

The present invention discloses liquid cleansing compositions comprising critical amounts (0.1-5% by wt.) of hydrogenated triglyceride of defined value to stabilize the compositions over a temperature range of 4° C. to 50° C. The solid hydrogenated triglycerides can be directly added into the surfactant base or be pre-mixed with other hydrophobic oils such as triglyceride oil or hydrocarbon oils (where they preferably comprise 40% or more of the mix sufficient to ensure desired crystallinity for stability). It is critical, however, that total amounts of hydrogenated glycerides in the final composition, regardless of source, be within specific amount range to ensure retention of viscosity after cold temperature storage (4° C. for one week). Use of such minimum amounts of saturated triglyceride (defined by IV 0 to less than 20) in liquid cleansing compositions, preferably in compositions comprising fatty acyl isethionate and amphoteric; or comprising acyl isethionate and alkanoyl glycinate is believed unknown.

In general, triglycerides are the main constituents of vegetable oils and animal fats. A triglyceride, also called triacylglycerol (TAG), is a chemical compound formed from one molecule of glycerol and three fatty acids. Hydrogenated triglycerides are the triglyceride oils produced after the contained unsaturated C=C double bonds are hydrogenated and converted into C—C single bonds. The schematic chemical structure of hydrogenated triglycerides is given below:

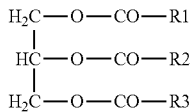

where R1, R2, R3 are saturated carboxylic acids which are esterified with glycerol to form saturated triacylglycerol (TAG) esters. The fatty acids in TAG commonly have chain lengths from 10-24, mostly including C10 (Capric acid), C12 (Lauric acid), C14 (Myristic acid), C16 (Palmitic acid), C18 (Stearic acid) and C20 (Arachidic acid) fatty acid. Naturally sourced vegetable oils and fats also contain substantial amount of monounsaturates such as C16:1 (Palmitoleic acid), C18:1 (Oleic acid) and polyunsaturated fatty acids such as C18:2 (Linoleic acid)) and C18:3 (Linolenic acid) and so on, depending on the source of oils and regions. In the oil and grease industry, the hydrogenated triglycerides are synthesized by catalyst induced addition reaction with hydrogen to remove the C=C double bonds in fatty acid chains. The degree of saturation in triglycerides can be quantified by the amount of contained C=C double bonds in the molecule. Conveniently, the Iodine Value (or "iodine adsorption value" or "IV number" or "iodine index") is often used in lipid chemistry, and is defined as the mass of iodine in grams that is consumed by 100 grams of a chemical substance. For triglycerides, a higher iodine value indicates more unsaturated double bonds in fatty acids. In an ideal case, a fully hydrogenated triglyceride should have Iodine value close to zero as it can not be further reacted with hydrogen. Also, by the definition of Iodine Value, this should be the case for all types of triglyceride oils.

Besides Iodine Value, the solid content (crystal percentage) is another frequently used parameter used to characterize hydrogenated triglycerides, whether added alone or as mixture. Thermal transition analysis (Differential Scanning calorimetry, DSC) is used to measure the contained crystal content by calculating the energy (enthalpy) needed to achieve phase transition of samples (melting for crystal phase or freezing for liquid phase). In DSC, the crystal percentage is calculated by the integrated melting (or freezing) peak of samples as compared to the fully hydrogenated samples of the same oils. At room temperature, the hydrogenated triglyceride (usually have melting point much higher than room temperature), would have 100% crystal percentage while liquid oils have 0% crystal percentage. Oil mixtures have a value somewhere in between.

There has been much work relating to use of hydrogenated triglycerides and structured oils in personal product composition. Some of the most relevant works are briefly listed as following:

EP 1,479,365 discloses benefit agent materials structured with crystalline material. U.S. Publication 2004/023569 A1 discloses non-bar compositions comprising crystalline wax structured benefit agent. U.S. 2004/0234467 A1 discloses compositions comprising structured benefit agent for deposition of hydrophilic benefit agent. EP 1,479,378 relates to bars with crystalline wax structured delivery vehicle.

U.S. 2004/0234468, U.S. 2004/0234469 and U.S. 2004/0234558 disclose structured premix to enhance delivery of hydrophobic agent.

WO 2004/017745 discloses mixing non-hydrogenated and hydrogenated oils for dispersed liquid oil or solid particles in fat phase for food compositions.

None of these references disclose compositions wherein specific critical amounts of hydrogenated triglyceride (delivered, preferably, as pure triglyceride, but also can be delivered as mixture with oils) are used in combination with defined fatty acids to stabilize liquid compositions, preferably those comprising a DEFI surfactant and amphoteric surfactant system, or DEFI surfactant and alkanoyl glycinate surfactant system, over low temperature storage conditions.

U.S. 2005/0281851 to Cap discloses cosmetic products (no liquid cleansing application) comprising vegetable oil blends and additional fatty acid where blends have iodine value range of 20-80, and where no applicable viscosity range is specified. There is no disclosure of use of 0.1-5% of fully hydrogenated triglyceride having IV 0 to <20 or of advantageous use for low temperature stability.

Unexpectedly, applicants have found that when specific range of hydrogenated triglyceride is used in liquid compositions comprising $C_{10}$-$C_{20}$ linear fatty acids, low temperature stability (as low as 4° C. for one week) is retained (>70% viscosity, preferably 75% or greater).

BRIEF DESCRIPTION OF INVENTION

The present invention relates to personal product composition with low temperature stability and retention of viscosity comprising:
(1) 1 to 40 wt %, preferably 5 to 40%, more preferably 10 to 35% of surfactants containing mixture of anionic, nonionic, zwitterionic surfactants and mixture of the above
(2) 0.5 to 10 wt % linear fatty acids with 10 to 20 carbons
(3) 0.1 to 5, preferably 0.5 to 4% wt % of hydrogenated triglyceride with IV number 20 or less, preferably 10 or less, and a melting temperature between 35 C to 80° C.;
wherein the hydrogenated triglyceride is introduced alone or as a mixture with other oils (where hydrogenated triglyceride preferably comprises 40% or more, preferably 50% or more of mixture)
wherein the said liquid cleanser composition is stable at low temperature and retains at least 70% of its original viscosity after being stored at 4° C. refrigerator for 7 days.

As noted, total hydrogenated triglyceride of IV 0 to less than 20 is delivered as pure solid, or mixture of solid in other oils.

The invention further relates to a method of stabilizing liquid composition at temperatures of 0° to 50° C., preferably 4 to 40° C. which method comprises utilizing the composition noted above.

In a preferred embodiment only the hydrogenated triglyceride of defined IV is used, and the amount used is 0.1 to 5%, preferably 0.5 to 4%, more preferably, 0.5 to 2.5%.

The viscosity results of products stored at 4° Celsius for 7 days are summarized in the examples. These clearly indicate that hydrogenated triglyceride oil, as claimed in the invention, can improve the low temperature stability of the liquid cleanser composition. For example, comparative example A (sunflower seed oil) having no hydrogenated triglyceride oil in the liquid, retained only 51.9% of the original viscosity (34800 cps vs. 73200 cps overnight viscosity) after being stored at 4° C. for 7 days. Liquids with the same surfactant composition as Comparative Example A, but containing the hydrogenated triglyceride oils of this invention were stable at low temperature, and maintained 80% or more of their original viscosity.

When used alone, the iodine value of the hydrogenated triglycerides is under 20, preferably less than 10, more preferably close to 0. Even in a mixture of hydrogenated triglycerides with other benefit oils, there is still required the presence of 0.1 to 5% (total composition) hydrogenated oil. Further, to ensure concentration of crystal content is sufficient to ensure low temperature stabilization, preferably hydrogenated triglyceride comprises 40% or more, preferably 50% or more of the mixture.

The use of such in liquid surfactant containing personal product compositions allows stabilization of liquid cleansing products at low temperature during storage and transportation.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to surfactant-containing liquid (also containing linear fatty acids) personal wash compositions (preferably aqueous based compositions having >30%, preferably 35% water) providing low temperature stability (retention of viscosity after cold temperature storage) using specific amount of hydrogenated (saturated) triglycerides having a defined degree of saturation. Specifically, when a defined hydrogenated triglyceride (defined by specific iodine value) is formulated with surfactants and other ingredients, the compositions will have precisely the right characteristics such that the low temperature stability of liquid formulations is retained. The hydrogenated triglycerides may be delivered as pure component (i.e., only triglycerides having defined IV range are used); or they may be delivered as pure ingredients in combination with other oils (i.e., oil which may have IV range outside defined range).

It is important, however, that there be present sufficient hydrogenated triglyceride component in the overall formulations such that formulations retain at least 70%, preferably 75% or greater, of their original formulation viscosity value after storage at 4° C. for 7 days. As noted, this results from the use of sufficient hydrogenated triglyceride, whether delivered in pure form or mixed with other oils. The hydrogenated oil (having IV number of less than 20, preferably 10 and less), should be used in the amount of 0.1 to 5%, preferably 0.5 to 4% by wt. total composition to obtain required low temperature stability characteristics noted in compositions of the invention.

In general, degree of saturation/hydrogenation may be characterized (1) by an iodine value which corresponds to that specific value for a particular oil; (2) by the concentration (percentage) of hydrogenated triglyceride crystal; and/or (3) by phase transition enthalpy. The invention is described in greater detail below.

The compositions in which the blends of the invention may be used comprise 1% by wt. to 40% by wt., preferably 5 to 40%, more preferably 10-35% by wt. surfactant. Surfactants may be anionic, nonionic amphoteric/zwitterionic, cationic or mixtures thereof. Examples of the many surfactants which may be used are set forth, for to example, in U.S. Pat. No. 6,395,690 to Tsaur.

Anionic may be aliphatic sulfonate (e.g., $C_8$-$C_{22}$ alkane or alkene sulfonate or aromatic sulfonate); alkyl sulfate (including alkyl and alkyl ether sulfate); sulfosuccinate; taurate; sarcosinates; sulfoacetate; alkyl phosphate.

Anionics may also be carboxylates and ether carboxylates. Another preferred class is $C_8$ to $C_{22}$ acyl isethionates. These esters are prepared by reacting alkali metal isethionate with mixed aliphatic fatty acids.

In a preferred embodiment of the invention, anionic surfactant comprises 50% or more of the total surfactant system of the composition of the invention.

Zwitterionic surfactants are broadly derivates of aliphatic quaternary ammonium, phosphonium and sulfonium compound in which aliphatic radicals are straight or branched chain, and wherein one of the aliphatic substituents contains 8 to 18 carbons and one contains an anionic group, e.g., carboxy, sulfonate, sulfate, phosphate or phosphonate.

Amphoteric surfactants include at least one acid group (e.g., carboxylic or sulphonic acid group). They include quaternary nitrogen and are quaternary amido acid. They typically include $C_7$ to $C_{18}$ alkyl or alkenyl group. Examples include betaines, amido betaines, sulphobetaines.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference. Preferred alkyl polysaccharides are alkylpolyglycosides.

Cationic surfactants are selected from the group consisting of: alkyl trimonnium chloride and methosulfate, and dialkyldimonnium chloride and methyl sulphate, and alkyl alkonium chloride and methyl sulphate and mixtures thereof. These surfactants contain $C_{12}$ to $C_{24}$ carbon atoms per alkyl chain. The most preferred cationic is selected from the group consisting of stearylalkonium chloride, stearyltrimonium chloride. Di-stearyl-dimonium chloride, and mixtures thereof.

A particularly preferred composition in which triglycerides of the invention may be used comprises 1-25 wt %, preferably 1- to 20 wt % DEFI (directly esterified fatty acid isethionate) and 1-15 wt % other synthetic cosurfactants especially betaine and glycinate cosurfactants.

In another preferred embodiment, the compositions may comprise a combination of a fatty acyl isethionate product and alkanoyl glycinate. An example of such system is described, for example, in U.S. Ser. No. 12/751,049 to Tsaur et al., filed Mar. 31, 2010, hereby incorporated by reference into the subject application.

A preferred fatty acyl isethionate product might comprise (in addition to other components) both pure fatty acyl isethionate surfactant (e.g., 40 to 80% of the product) as well as free fatty acid and/or fatty acid salt (e.g., 15 to 50%). In addition, in such preferred product, greater than 20%, preferably greater than 25% of the fatty acyl isethionate and less than 45 wt. % may be of chain length greater than or equal to $C_{16}$; and greater than 50%, preferably greater than 60% of the free fatty acid/soap may be of chain length $C_{16}$ to $C_{20}$.

The fatty acyl isethionate surfactant component is typically prepared by the reaction of an isethionates salt such as alkali metal isethionates and an aliphatic fatty acid having 8 to 20 carbon atoms and Iodine Value (measuring degree of unsaturation) of less than 20 g, for example:

HOR$_1$SO$_3$M→RCOOR$_1$SO$_3$H where $R_1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Depending on the processing conditions used, the resulting fatty acyl isethionate product can be a mixture of 40 to 80% by weight of fatty acyl isethionates (which formed from the reaction) and 50 to about 15 wt. %, typically 40 to 20 wt. % of free fatty acids. In addition, product may contain isethionates salts which are present typically at levels less than 5 wt. %, and traces (less than 2 wt. %) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) preferably should have more than 20 wt. %, preferably more than 25%, but no more than 40% wt., preferably 35% (on basis of fatty acyl isethionates reaction product) of fatty acyl group with 16 or greater carbon atoms to provide both lather and mildness of the resulting fatty acyl isethionate product. These longer chain fatty acyl isethionate surfactants and fatty acids, i.e. fatty acyl group and fatty acid with 16 or more carbons, form insoluble surfactant/fatty acid crystals typically in water at ambient temperatures. While not wishing to be bound by theory, it is believed that long chain fatty acyl isethionate surfactants in the product together with free long chain fatty acids in the product contribute to the mildness of the fatty acyl isethionate product for skin cleanser applications.

Examples of commercial fatty acyl isethionate products that are particularly useful in the subject invention are DEFI flakes and Dove® cleansing bar noodles produced by Unilever. DEFI (Direct Esterification of Fatty Isethionate) flakes typically contain about 68 to 80 wt. % of sodium fatty acyl isethionate and 15 to 30 wt. % free fatty acid. More than 25 wt. % and no more than 35% of fatty acyl group of the resulting fatty acyl isethionate have 16 to 18 carbon atoms. Dove® cleansing bar noodles are mixtures of DEFI flakes described above and long chain (mainly $C_{16}$ and $C_{18}$) fatty acid and fatty soap which contain about 40 to 55 wt. % of fatty acyl isethionate and 30 to 40 wt. % of fatty acid and fatty soap. Due to the high level of long chain (16 or more carbons) fatty acyl isethionate and fatty acid, these preferred fatty acyl isethionate surfactant products are extremely mild and have very good emollient benefits to the skin.

The alkanoyl glycinate used is typically a salt of alkanoyl glycinate. Preferred salts include alkali metal salts of alkanoyl glycinate such as sodium cocoyl glycinate and/or alkanolamino salts such as trialkanolamine salt of glycinate.

As is well know in the art, alkanoyl is the systematic name for group:

which is also known as an acyl group. Thus, alkanoyl glycinate is the same as acyl glycinate and represents a molecule, for example, where salt of acyl group, such as for example:

(where R may be, for example, $C_8$-$C_{24}$, preferably $C_{12}$-$C_{20}$) is combined with glycine:

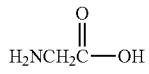

to form the alkanoyl glycinate (an amide where alkanoyl group bonds to nitrogen to form amide):

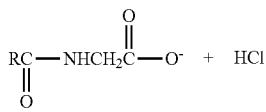

The above reaction may be conducted, for example, by an acid chloride route where R group on the acyl chloride is used to define the R group on the final alkanoyl glycinate (e.g., cocoyl glycinate if R in the acyl group is a cocoyl group).

In one embodiment, composition of the invention may comprise $C_{10}$ to $C_{20}$ straight chain fatty alcohol, for example lauryl alcohol.

A second component of the invention is $C_{10}$ to $C_{20}$ linear fatty acids. These typically can cause instability in liquid compositions, particularly those stored in cold climates. Compositions of the invention comprise 0.5 to 10%, preferably 1% to 8% by wt. of said fatty acids. The linear fatty acids of the invention may be introduced directly or may be introduced as part of the DEFI product which product contains both acyl isethionate and fatty acid components.

A third required component of the subject invention (besides (1) surfactants and (2) linear fatty acid) is hydrogenated triglyceride oil. More specifically, the invention requires that there be used from 0.1 to 5% by wt. (total content whether delivered in pure form, or as a mixture), of hydrogenated triglyceride oil which has IV number of less than 20, preferably 10 or less and a melting temperature between 35° to 80° C. (reflective of level of saturation).

As indicated, the hydrogenated triglycerides with defined IV value and concentration in the composition are required to give the claimed low temperature stability and viscosity retention. However, as also noted, the hydrogenated triglycerides can be delivered in combination with other oils (vegetable oils such as soybean oil or sunflower seed oil; or hydrocarbon oils such as mineral oil or petrolatum jelly). Where the triglyceride oil has a much higher IV number (for example, pure soybean oil has IV about 120-140), the IV number of a mixture of such oils with hydrogenated triglycerides may be much higher than 20 (because of the high level polyunsaturated fatty acids). However, as long as there is present at least 0.1 to 5% of the pure hydrogenated triglyceride in the composition (providing required crystallinity), such that the composition retains >70% of original viscosity, low temperature instability is controlled.

In a second embodiment of the invention, the invention relates to a method of stabilizing liquid composition which can be stored at a temperature of as low as 4° C. for one week which method comprises using a composition comprising:
  a. 1 to 40%, preferably 5 to 35% by wt. surfactant as defined above;
  b. 0.5 to 10% linear fatty acid of chain length $C_{10}$-$C_{20}$; and
  c. 0.1 to 5% fully hydrogenated triglyceride of IV 0 to <20 and having melting temperature between 35° to 80° C., wherein said hydrogenated oil is introduced as pure oil (typically oil with IV of 0 to <20, preferably 0-10, are solid rather than liquid) or a mixture of pure oil and other oils (as long as final content of hydrogenated oil in final formulation is within defined window).

Protocol

1. Sample Preparation

Liquids were prepared by mixing all the ingredients except glydant plus, perfume, citric acid and EDTA at 70-75° C. for 30 to 50 minutes until all the solids such as lauric acid, hydrogenated triglyceride and fatty acyl isethionate surfactant product dissolved to form a uniform mix. Fatty isethionate product is fatty acyl isethionate products manufactured by Unilever. It contain about 50 wt % of fatty acyl isethionate surfactant with about 30% of the fatty acyl group equal to or longer than 16 carbon, and about 35 wt % of linear fatty acid/linear fatty soap in which about 79 wt % of the fatty acid/fatty soap have 16 to 20 carbons. Hydrogenated triglyceride oil (with IV<20) was added as is to the mixing tank; or was added as a premix with other triglyceride oil by mixing the hydrogenated triglyceride oil with other oils such as sunflower seed oil above the melting temperature of the hydrogenated triglyceride oils. The mixture was then cooled below 40° C. Rest of the ingredients were added and mixed for another 10 to 20 minutes. The sample was poured and saved in 4 ounce jar for viscosity measurement. One was stored at room temperature (20 to 25° C.) and the other was placed in a 4° C. refrigerator for 7 days.

2. Storage Stability Evaluation

The stability of personal wash prototypes were evaluated by viscosity. The viscosity of each sample was measured using Brookfield viscometer (0.05 rpm, #5 spindle at 20 to 25° C. ambient temperature) and the results are also summarized in the table. Overnight viscosity was determined after the sample was aged at room temperature (20-25° C.) overnight. 4° C., 7 days storage viscosity was determined after the sample was aged at room temperature (20 to 25° C.) for 20 to 24 hours after the sample had been stored at 4° C. for 7 days.

3. Thermal Analysis

The melting point and phase transition profile of oil blends in this invention was characterized by Differential Scanning calorimetry (DSC) using TA instruments Q-1000. Typically a 5-10 mg of oil blend was heated from room temperature up to 100° C. and cooled down to room temperature or lower at ramp rate of 3° C./minute. The phase transition energy was calculated by integrating the exotherm and endotherm curves using software Universal Analysis 2000 and averaged.

4. Oil Blends Premixing

The hydrogenated triglycerides in this invention are from either pure fully hydrogenated triglyceride, partially hydrogenated triglycerides or mixed with other benefit agents. For oil blends, the samples are heated and stirred at temperature above melting point of any ingredients. If possible, rather than using partially hydrogenation process starting from triglyceride oils (which hydrogenation may be difficult to control), simply mix vegetable oil with fully hydrogenated vegetable fats (at temperature above melting point of either component) at a ratio required to give required concentration of crystal content and low temperature stability to liquid cleansing formulations.

This, in turn, can be controlled by noting the strong linear correlation which applicants measured between iodine value (measure of lipid saturation) and the crystal content in the simple mixture of fully hydrogenated oils to regular oils (RBD oil, commonly called in industry refers to refined bleached and deodorized) or partially hydrogenated oil.

Examples 1 to 5 and Comparative A

The viscosity results of products stored at 4° Celsius after overnight and 7 days are summarized in the table. The results clearly indicate that hydrogenated triglyceride oil as claimed in the invention can improve the low temperature stability of the liquid cleanser composition. For example, in Comparative Example A, without any hydrogenated triglyceride oil (only sunflower seed oil), the liquid only retained 51.9% of the original viscosity (34800 cps vs. 73200 cps overnight viscosity) after being stored at 4° C. for 7 days. Liquids, with same surfactant composition as Comparative Example A, containing hydrogenated triglyceride oils of this invention (in addition to some soybean soybean or sunflower oil), are stable at low temperature, and maintain 80% or more of their original viscosity.

TABLE 1

Effect of Hydrogenated Triglycerides on liquid low temperature stability

| Example | 1 | 2 | 3 | 4 | Comparative A |
|---|---|---|---|---|---|
| Fatty acyl isethionate surfactant product* | 2 | 2 | 2 | 2 | 2 |
| Betaine | 4 | 4 | 4 | 4 | 4 |
| Na laureth(1EO) sulfate | 3.5 | 3.5 | 3.5 | 3.5 | 3.5 |
| Na cocoyl glycinate | 2.5 | 2.5 | 2.5 | 2.5 | 2.5 |
| Lauric acid | 1.75 | 1.75 | 1.5 | 1.5 | 1.75 |
| Pure Gel | 3.85 | 3.85 | 3.5 | 3.5 | 3.85 |
| Cationic Guar | 0.2 | 0.2 | 0.2 | 0.2 | 0.2 |
| Glycerin | 6 | 6 | 6 | 6 | 6 |
| Soybean oil | — | — | 3 | 3.75 | — |
| Sunflower seed oil | 3 | 3 | — | — | 5 |
| fully hydrogenated soybean oil (IV 0 to <20) | 2 | 2 | — | 1.25 | — |
| Fully hydrogenated Palm Kernel oil (Hydrokote 112 from Abetec) | — | — | 2 | — | — |
| hydrogenated oil addition method | added separately | added as premix | added separately | added as premix | — |
| glydant plus | 0.2 | 0.2 | 0.2 | 0.2 | 0.2 |
| citric acid | 0.09 | 0.09 | 0.09 | 0.09 | 0.09 |
| Perfume | 1.1 | 1.1 | 1.1 | 1.1 | 1.1 |
| EDTA | 0.05 | 0.05 | 0.05 | 0.05 | 0.05 |
| deionized water | to 100 | to 100 | to 100 | to 100 | to 100 |
| overnight viscosity (centipoise) | 91600 | 103000 | 84800 | 60000 | 73200 |
| 4° C., 7 days storage viscosity (centipoise) | 106000 | 123200 | 73600 | 48000 | 38000 |
| % of original viscosity | 115.7 | 119.6 | 86.8 | 80.0 | 51.9 |

*It contain about 50 wt % of fatty acyl isethionate surfactant with about 30% of the fatty acyl group equal to or longer than 16 carbon, and about 35 wt % of linear fatty acid/linear fatty soap in which about 79 wt % of the fatty acid/fatty soap have 16 to 20 carbons.

Examples 5-6 and Comparative B

Table below are additional examples of hydrogenated oils of defined IV in different surfactant compositions. As seen from Examples 5 and 6 relative to Comparative B, use of hydrogenated oil significantly enhanced stability.

TABLE 2

Effect of Hydrogenated Triglycerides on Liquid low temperature stability

| Example | B | 5 | 6 |
|---|---|---|---|
| Fatty acyl isethionate surfactant product* | 14 | 12 | 12 |
| Betaine | 3.5 | 3.5 | 3.5 |
| Na laureth(1EO) sulfate | 5.8 | 8.0 | 8.0 |
| Lauric acid | 2.7 | 2.4 | 2.4 |
| Cationic Guar | 0.2 | 0.2 | 0.2 |
| Glycerin | 3 | 1 | 1 |
| Soybean oil | 10 | 0.5 | 1.2 |
| fully hydrogenated soybean oil (IV 0 to <20) | — | 2 | 0.8 |
| hydrogenated soybean oil addition method | — | separately | separately |
| lauryl alcohol | — | 0.75 | 0.75 |
| glydant plus | 0.1 | 0.13 | 0.13 |
| Perfume | 1.1 | 1.1 | 1.1 |
|  | to 100 | to 100 | to 100 |
| EDTA | 0.05 | 0.047 | 0.047 |
| Overnight viscosity (centipoise) | 180000 | 140000 | 133000 |
| 4° C., 7 day storage viscosity (centipoise) | 52000 | 148000 | 116000 |
| % of original viscosity | 28.9 | 105.7 | 87.2 |

*It contain about 50 wt % of fatty acyl isethionate surfactant with about 30% of the fatty acyl group equal to or longer than 16 carbon, and about 35 wt % of linear fatty acid/linear fatty soap in which about 79 wt % of the fatty acid/fatty soap have 16 to 20 carbons.

The invention claimed is:

1. A liquid cleanser composition for low temperature stability and retention of viscosity comprising:
    1) 5 to 40 wt % of a surfactant system comprising surfactants selected from the group consisting of anionic, nonionic, and zwitterionic surfactants and mixture of the above, wherein said surfactant system comprises 50% or more anionic surfactant
    2) 0.5 to 10 wt % linear fatty acids with 10 to 20 carbons
    3) 0.1 to 5 wt % of hydrogenated triglyceride with IV number 0 to less than 20, and a melting temperature between 35° C. to 80° C.;
    wherein said hydrogenated triglyceride is added either alone or as a mixture of hydrogenated triglyceride with other triglycerides wherein the hydrogenated triglycerides comprise 40% or more of the mixture
    wherein, because of use of hydrogenated triglyceride alone or as 40% or more of mixture of triglycerides, the said liquid cleanser composition is stable and retains at least 70% of its original viscosity after being stored at 4° C. refrigerator for 7 days.

2. A composition according to claim 1 wherein surfactant system comprises fatty acyl isethionate product surfactant and alkanoyl glycinate surfactant.

3. A composition according to claim 1 wherein IV of hydrogenated triglycerides is 10 or less.

4. A composition according to claim 1 wherein such other triglyceride oil is soybean oil or sunflower seed oil.

* * * * *